(12) United States Patent
Llanos et al.

(10) Patent No.: US 7,261,735 B2
(45) Date of Patent: Aug. 28, 2007

(54) LOCAL DRUG DELIVERY DEVICES AND METHODS FOR MAINTAINING THE DRUG COATINGS THEREON

(75) Inventors: Gerard H. Llanos, Stewartsville, NJ (US); David Christian Lentz, Weston, FL (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/887,464

(22) Filed: Jun. 22, 2001

(65) Prior Publication Data

US 2002/0165608 A1 Nov. 7, 2002

Related U.S. Application Data

(63) Continuation-in-part of application No. 09/850,482, filed on May 7, 2001.

(51) Int. Cl.
*A61F 2/06* (2006.01)
(52) U.S. Cl. .................. 623/1.46; 623/1.42; 623/1.44
(58) Field of Classification Search ............ 604/95.03, 604/96.01, 101.02, 103.02, 51–53, 500, 890.1, 604/891.1; 623/11, 1.42–1.48, 1.16; 512/291, 512/56, 378, 466, 824, 521, 18, 456, 763, 512/44, 2, 93.2, 964; 424/122, 423–424, 424/240.22
See application file for complete search history.

(56) References Cited

U.S. PATENT DOCUMENTS

| 3,585,707 | A | 6/1971 | Stevens ................ 29/426.2 |
| 3,657,744 | A | 4/1972 | Ersek |
| 3,929,992 | A | 12/1975 | Seghal et al. ........... 424/122 |
| 3,932,627 | A | 1/1976 | Margraf |
| 3,959,078 | A | 5/1976 | Guire ................... 530/350 |
| 4,292,965 | A | 10/1981 | Nash et al. |
| 4,366,819 | A | 1/1983 | Kaster ................... 606/153 |
| 4,368,736 | A | 1/1983 | Kaster ................... 606/153 |
| 4,441,216 | A | 4/1984 | Ionescu et al. |
| 4,503,569 | A | 3/1985 | Dotter |
| 4,553,545 | A | 11/1985 | Maass et al. |
| 4,580,568 | A | 4/1986 | Gianturco |
| 4,613,665 | A | 9/1986 | Larm |
| 4,624,257 | A | 11/1986 | Berggren et al. ......... 606/153 |
| 4,655,771 | A | 4/1987 | Wallsten |
| 4,722,906 | A | 2/1988 | Guire ................... 436/501 |

(Continued)

FOREIGN PATENT DOCUMENTS

DE  3205942 A1  9/1983

(Continued)

OTHER PUBLICATIONS

PCT International Search Report, dated Oct. 22, 2002, for PCT Int'l. Appln. No. PCT/US02/19889.

(Continued)

*Primary Examiner*—Patricia Bianco
*Assistant Examiner*—Camtu Nguyen
(74) *Attorney, Agent, or Firm*—Carl J. Evens (57) ABSTRACT

Local drug delivery medical devices are utilized to deliver therapeutic dosages of drugs, agents or compounds directly to the site where needed. The local drug delivery medical devices utilize various materials and coating methodologies to maintain the drugs, agents or compounds on the medical device until delivered and positioned.

3 Claims, 4 Drawing Sheets

U.S. PATENT DOCUMENTS

| | | |
|---|---|---|
| 4,733,665 A | 3/1988 | Palmaz |
| 4,739,665 A | 4/1988 | Nordvall ................... 73/862.08 |
| 4,739,762 A | 4/1988 | Palmaz |
| 4,776,337 A | 10/1988 | Palmaz |
| 4,800,882 A | 1/1989 | Gianturco |
| 4,810,784 A | 3/1989 | Larm ......................... 536/20 |
| 4,856,516 A | 8/1989 | Hillstead |
| 4,872,867 A | 10/1989 | Joh |
| 4,886,062 A | 12/1989 | Wiktor |
| 4,907,336 A | 3/1990 | Gianturco |
| 4,916,193 A | 4/1990 | Tang et al. |
| 4,917,090 A | 4/1990 | Berggren et al. ............ 606/153 |
| 4,917,091 A | 4/1990 | Berggren et al. ............ 606/153 |
| 4,954,126 A | 9/1990 | Wallsten |
| 4,969,458 A | 11/1990 | Wiktor |
| 4,990,131 A | 2/1991 | Dardik |
| 4,990,155 A | 2/1991 | Wilkoff |
| 4,994,071 A | 2/1991 | MacGregor |
| 5,015,253 A | 5/1991 | MacGregor |
| 5,035,706 A | 7/1991 | Gianturco |
| 5,041,100 A | 8/1991 | Rowland et al. |
| 5,041,126 A | 8/1991 | Gianturco |
| 5,045,072 A | 9/1991 | Castillo et al. ............. 604/529 |
| 5,049,132 A | 9/1991 | Shaffer et al. |
| 5,049,403 A | 9/1991 | Larm et al. .................. 427/2.1 |
| 5,053,048 A | 10/1991 | Pinchuk |
| 5,061,275 A | 10/1991 | Wallsten et al. |
| 5,061,750 A | 10/1991 | Feijen et al. |
| 5,064,435 A | 11/1991 | Porter |
| 5,092,877 A | 3/1992 | Pinchuk |
| 5,102,417 A | 4/1992 | Palmaz |
| 5,104,404 A | 4/1992 | Wolff |
| 5,116,365 A | 5/1992 | Hillstead |
| 5,122,154 A | 6/1992 | Rhodes |
| 5,131,908 A | 7/1992 | Dardik et al. |
| 5,133,732 A | 7/1992 | Wiktor |
| 5,134,192 A | 7/1992 | Feijen et al. |
| 5,135,536 A | 8/1992 | Hillstead |
| 5,163,952 A | 11/1992 | Froix |
| 5,163,958 A | 11/1992 | Pinchuk |
| 5,171,262 A | 12/1992 | MacGregor |
| 5,176,660 A | 1/1993 | Truckai |
| 5,178,618 A | 1/1993 | Kandarpa |
| 5,180,366 A | 1/1993 | Woods |
| 5,182,317 A | 1/1993 | Winters et al. |
| 5,185,408 A | 2/1993 | Tang et al. |
| 5,192,307 A | 3/1993 | Wall |
| 5,195,984 A | 3/1993 | Schatz |
| 5,213,576 A | 5/1993 | Abiuso et al. |
| 5,217,483 A | 6/1993 | Tower |
| 5,222,971 A | 6/1993 | Willard et al. |
| 5,226,913 A | 7/1993 | Pinchuk |
| 5,229,172 A | 7/1993 | Cahalan et al. ............. 427/536 |
| 5,234,456 A | 8/1993 | Silvestrini |
| 5,246,445 A | 9/1993 | Yachia et al. |
| 5,254,107 A | 10/1993 | Soltesz ........................ 604/525 |
| 5,258,020 A | 11/1993 | Froix |
| 5,258,021 A | 11/1993 | Duran |
| 5,262,451 A | 11/1993 | Winters et al. |
| 5,266,073 A | 11/1993 | Wall |
| 5,272,012 A * | 12/1993 | Opolski ................... 428/423.1 |
| 5,275,622 A | 1/1994 | Lazarus et al. |
| 5,282,823 A | 2/1994 | Schwartz et al. |
| 5,282,824 A | 2/1994 | Gianturco |
| 5,283,257 A | 2/1994 | Gregory et al. |
| 5,288,711 A | 2/1994 | Mitchell et al. |
| 5,290,305 A | 3/1994 | Inoue |
| 5,292,331 A | 3/1994 | Boneau |
| 5,292,802 A | 3/1994 | Rhee et al. |
| 5,304,121 A | 4/1994 | Sahatjian |
| 5,304,200 A | 4/1994 | Spaulding |
| 5,306,250 A | 4/1994 | March et al. |
| 5,308,641 A | 5/1994 | Cahalan et al. ............... 427/2.1 |
| 5,308,862 A | 5/1994 | Ohlstein |
| 5,308,889 A | 5/1994 | Rhee et al. |
| 5,314,444 A | 5/1994 | Gianturco |
| 5,314,472 A | 5/1994 | Fontaine |
| 5,328,471 A | 7/1994 | Slepian |
| 5,334,301 A | 8/1994 | Heinke et al. |
| 5,336,518 A | 8/1994 | Narayanan et al. |
| 5,338,770 A | 8/1994 | Winters et al. |
| 5,342,348 A | 8/1994 | Kaplan |
| 5,342,387 A | 8/1994 | Summers |
| 5,342,621 A | 8/1994 | Eury |
| 5,350,800 A | 9/1994 | Verhoeven et al. ........ 525/54.2 |
| 5,354,257 A | 10/1994 | Roubin et al. |
| 5,354,308 A | 10/1994 | Simon et al. |
| 5,356,433 A | 10/1994 | Rowland et al. |
| 5,366,504 A | 11/1994 | Andersen et al. |
| 5,368,566 A | 11/1994 | Crocker |
| 5,370,683 A | 12/1994 | Fontaine |
| 5,370,691 A | 12/1994 | Samson |
| 5,375,612 A | 12/1994 | Cottenceau et al. |
| 5,376,112 A | 12/1994 | Duran |
| 5,380,299 A | 1/1995 | Fearnot et al. |
| 5,382,261 A | 1/1995 | Palmaz |
| 5,383,928 A | 1/1995 | Scott et al. |
| 5,387,235 A | 2/1995 | Chuter |
| 5,389,106 A | 2/1995 | Tower |
| 5,393,772 A | 2/1995 | Yue et al. |
| 5,395,390 A | 3/1995 | Simon et al. |
| 5,397,355 A | 3/1995 | Marin et al. |
| 5,403,341 A | 4/1995 | Solar |
| 5,405,377 A | 4/1995 | Cragg |
| 5,409,696 A | 4/1995 | Narayanan et al. |
| 5,411,549 A | 5/1995 | Peters |
| 5,415,619 A | 5/1995 | Lee et al. |
| 5,415,938 A | 5/1995 | Cahalan et al. ............. 428/409 |
| 5,419,760 A | 5/1995 | Narciso, Jr. |
| D359,802 S | 6/1995 | Fontaine |
| 5,421,955 A | 6/1995 | Lau |
| 5,423,885 A | 6/1995 | Williams |
| 5,429,618 A | 7/1995 | Keogh |
| 5,429,634 A | 7/1995 | Narcisco |
| 5,439,446 A | 8/1995 | Barry |
| 5,441,515 A | 8/1995 | Khosravi et al. |
| 5,441,516 A | 8/1995 | Wang et al. |
| 5,441,947 A | 8/1995 | Dodge et al. |
| 5,443,458 A | 8/1995 | Eury |
| 5,443,477 A | 8/1995 | Marin et al. |
| 5,443,496 A | 8/1995 | Schwartz et al. |
| 5,443,498 A | 8/1995 | Fontaine |
| 5,443,500 A | 8/1995 | Sigwart |
| 5,447,724 A | 9/1995 | Heimus et al. |
| 5,449,372 A | 9/1995 | Schmaltz et al. |
| 5,449,373 A | 9/1995 | Pinchasik et al. |
| 5,449,382 A | 9/1995 | Dayton |
| 5,464,450 A | 11/1995 | Buscemi et al. |
| 5,464,650 A | 11/1995 | Berg et al. |
| 5,486,357 A | 1/1996 | Narayanan |
| 5,496,365 A | 3/1996 | Sgro |
| 5,500,013 A | 3/1996 | Buscemi et al. |
| 5,510,077 A | 4/1996 | Dinh et al. |
| 5,516,781 A | 5/1996 | Morris et al. |
| 5,523,092 A | 6/1996 | Hanson et al. |
| 5,527,354 A | 6/1996 | Fontaine et al. |
| 5,545,208 A | 8/1996 | Wolff et al. |
| 5,551,954 A | 9/1996 | Buscemi et al. |
| 5,554,182 A | 9/1996 | Dinh et al. |
| 5,554,954 A | 9/1996 | Takahashi |
| 5,556,413 A | 9/1996 | Lam |
| 5,562,922 A | 10/1996 | Lambert |
| 5,563,146 A | 10/1996 | Morris et al. |
| 5,569,197 A | 10/1996 | Helmus et al. |

| | | | | | | |
|---|---|---|---|---|---|---|
| 5,569,295 A | 10/1996 | Lam | | 5,824,048 A | 10/1998 | Tuch |
| 5,571,166 A | 11/1996 | Dinh et al. | | 5,824,049 A | 10/1998 | Ragheb et al. |
| 5,574,059 A | 11/1996 | Regunathan et al. | | 5,833,651 A * | 11/1998 | Donovan et al. ............ 604/509 |
| 5,578,075 A | 11/1996 | Dayton | | 5,837,008 A | 11/1998 | Berg et al. |
| 5,580,873 A | 12/1996 | Bianco et al. | | 5,837,313 A * | 11/1998 | Ding et al. ................ 427/2.21 |
| 5,580,874 A | 12/1996 | Bianco et al. | | 5,843,172 A | 12/1998 | Yan |
| 5,591,140 A | 1/1997 | Narayanan et al. | | 5,849,034 A | 12/1998 | Schwartz |
| 5,591,197 A | 1/1997 | Orth et al. | | 5,851,217 A | 12/1998 | Wolff et al. |
| 5,591,224 A | 1/1997 | Schwartz et al. | | 5,851,231 A | 12/1998 | Wolff et al. |
| 5,591,227 A | 1/1997 | Dinh et al. | | 5,858,990 A | 1/1999 | Walsh |
| 5,599,352 A | 2/1997 | Dinh et al. | | 5,861,027 A | 1/1999 | Trapp |
| 5,603,722 A | 2/1997 | Phan et al. | | 5,865,814 A | 2/1999 | Tuch |
| 5,605,696 A | 2/1997 | Eury et al. | | 5,871,535 A | 2/1999 | Wolff et al. |
| 5,607,463 A | 3/1997 | Schwartz et al. | | 5,873,904 A | 2/1999 | Ragheb et al. |
| 5,607,475 A | 3/1997 | Cahalan et al. | | 5,876,433 A | 3/1999 | Lunn |
| 5,609,629 A | 3/1997 | Fearnot et al. | | 5,879,697 A | 3/1999 | Ding et al. |
| 5,620,984 A | 4/1997 | Bianco et al. | | 5,882,335 A | 3/1999 | Leone et al. |
| 5,621,102 A | 4/1997 | Bianco et al. | | 5,883,651 A * | 3/1999 | Thiel et al. .................. 347/71 |
| 5,622,975 A | 4/1997 | Singh et al. | | 5,891,108 A | 4/1999 | Leone et al. |
| 5,624,411 A | 4/1997 | Tuch | | 5,900,246 A | 5/1999 | Lambert |
| 5,628,785 A | 5/1997 | Schwartz et al. | | 5,902,266 A | 5/1999 | Leone et al. |
| 5,629,077 A | 5/1997 | Turnlund et al. | | 5,924,997 A | 7/1999 | Campbell .................... 600/549 |
| 5,629,315 A | 5/1997 | Bianco et al. | | 5,951,586 A | 9/1999 | Berg et al. |
| 5,632,763 A | 5/1997 | Glastra | | 5,957,971 A | 9/1999 | Schwartz |
| 5,632,840 A | 5/1997 | Campbell | | 5,972,027 A | 10/1999 | Johnson |
| 5,637,113 A | 6/1997 | Tartaglia et al. | | 5,976,534 A | 11/1999 | Hart et al. |
| 5,643,312 A | 7/1997 | Fischell et al. | | 5,977,163 A | 11/1999 | Li et al. |
| 5,643,939 A | 7/1997 | Ohlstein | | 5,980,553 A | 11/1999 | Gray et al. |
| 5,646,160 A | 7/1997 | Morris et al. | | 5,980,566 A | 11/1999 | Alt et al. |
| 5,648,357 A | 7/1997 | Bianco et al. | | 5,980,972 A | 11/1999 | Ding |
| 5,649,952 A | 7/1997 | Lam | | 5,981,568 A | 11/1999 | Kunz et al. |
| 5,649,977 A | 7/1997 | Campbell | | 5,985,307 A | 11/1999 | Hanson et al. |
| 5,651,174 A | 7/1997 | Schwartz et al. | | 5,993,972 A * | 11/1999 | Reich et al. ............. 428/423.1 |
| 5,652,243 A | 7/1997 | Bianco et al. | | 5,997,468 A | 12/1999 | Wolff et al. |
| 5,653,992 A | 8/1997 | Bezwada et al. | | 6,004,346 A | 12/1999 | Wolff et al. |
| 5,662,609 A | 9/1997 | Slepian | | 6,039,721 A | 3/2000 | Johnson et al. |
| 5,665,728 A | 9/1997 | Morris et al. | | 6,059,813 A | 5/2000 | Vrba et al. |
| 5,669,924 A | 9/1997 | Shaknovich | | 6,071,305 A | 6/2000 | Brown et al. |
| 5,670,506 A | 9/1997 | Leigh et al. | | 6,074,659 A | 6/2000 | Kunz et al. |
| 5,674,242 A | 10/1997 | Phan et al. | | 6,080,190 A | 6/2000 | Schwartz |
| 5,679,400 A | 10/1997 | Tuch | | 6,096,070 A | 8/2000 | Ragheb et al. |
| 5,679,659 A | 10/1997 | Verhoeven et al. | | 6,099,562 A | 8/2000 | Ding et al. ................. 623/1.46 |
| 5,693,085 A | 12/1997 | Buirge et al. | | 6,120,536 A * | 9/2000 | Ding et al. ................. 623/1.43 |
| 5,697,967 A | 12/1997 | Dinh et al. | | 6,136,798 A | 10/2000 | Cody et al. |
| 5,697,971 A | 12/1997 | Fischell et al. | | 6,140,127 A | 10/2000 | Sprague |
| 5,700,286 A | 12/1997 | Tartaglia et al. | | 6,146,358 A | 11/2000 | Rowe |
| 5,707,385 A | 1/1998 | Williams | | 6,153,252 A | 11/2000 | Hossainy et al. |
| 5,709,874 A | 1/1998 | Hanson et al. | | 6,171,232 B1 | 1/2001 | Papandreou et al. |
| 5,725,549 A | 3/1998 | Lam | | 6,171,609 B1 | 1/2001 | Kunz |
| 5,725,567 A | 3/1998 | Wolff et al. | | 6,177,272 B1 | 1/2001 | Nabel et al. |
| 5,728,150 A | 3/1998 | McDonald et al. | | 6,179,817 B1* | 1/2001 | Zhong ........................ 604/265 |
| 5,728,420 A | 3/1998 | Keogh | | 6,214,901 B1* | 4/2001 | Chudzik et al. ............. 523/113 |
| 5,731,326 A | 3/1998 | Hart et al. | | 6,240,616 B1 | 6/2001 | Yan |
| 5,733,327 A | 3/1998 | Igaki et al. | | 6,245,026 B1 | 6/2001 | Campbell et al. ........... 600/549 |
| 5,733,920 A | 3/1998 | Mansuri et al. | | 6,254,632 B1 | 7/2001 | Wu et al. |
| 5,733,925 A | 3/1998 | Kunz et al. | | 6,254,634 B1* | 7/2001 | Anderson et al. ........... 623/1.42 |
| 5,735,897 A | 4/1998 | Buirge | | 6,258,121 B1 | 7/2001 | Yang et al. |
| 5,739,138 A | 4/1998 | Bianco et al. | | 6,268,390 B1 | 7/2001 | Kunz |
| 5,755,734 A | 5/1998 | Richter et al. | | 6,273,913 B1* | 8/2001 | Wright et al. ............... 604/265 |
| 5,769,883 A | 6/1998 | Buscemi et al. | | 6,284,305 B1* | 9/2001 | Ding et al. ................. 427/2.28 |
| 5,776,184 A | 7/1998 | Tuch | | 6,287,320 B1 | 9/2001 | Slepian |
| 5,780,476 A | 7/1998 | Underiner et al. | | 6,287,628 B1 | 9/2001 | Hossainy et al. |
| 5,782,908 A | 7/1998 | Cahalan et al. | | 6,299,604 B1 | 10/2001 | Ragheb et al. |
| 5,788,979 A | 8/1998 | Alt | | 6,306,144 B1* | 10/2001 | Sydney et al. .............. 606/108 |
| 5,792,772 A | 8/1998 | Bianco et al. | | 6,306,166 B1 | 10/2001 | Barry et al. |
| 5,798,372 A | 8/1998 | Davies et al. | | 6,306,176 B1 | 10/2001 | Whitbourne |
| 5,799,384 A | 9/1998 | Schwartz et al. | | 6,306,421 B1 | 10/2001 | Kunz et al. |
| 5,800,507 A | 9/1998 | Schwartz | | 6,309,380 B1 | 10/2001 | Larson et al. |
| 5,800,508 A | 9/1998 | Goicoechea et al. | | 6,309,660 B1 | 10/2001 | Hsu et al. |
| 5,807,861 A | 9/1998 | Klein et al. | | 6,313,264 B1 | 11/2001 | Caggiano et al. |
| 5,811,447 A | 9/1998 | Kunz et al. | | 6,375,676 B1* | 4/2002 | Cox ........................... 604/265 |
| 5,820,917 A | 10/1998 | Tuch | | 6,379,382 B1* | 4/2002 | Yang ......................... 623/1.42 |
| 5,820,918 A | 10/1998 | Ronan et al. | | 6,387,121 B1* | 5/2002 | Alt ............................ 623/1.42 |

| | | | | |
|---|---|---|---|---|
| 6,403,635 | B1 * | 6/2002 | Kinsella et al. | 514/449 |
| 6,407,067 | B1 * | 6/2002 | Schafer | 514/19 |
| 6,425,898 | B1 | 7/2002 | Wilson et al. | 606/108 |
| 6,429,232 | B1 * | 8/2002 | Kinsella et al. | 623/1.15 |
| 6,713,119 | B2 | 3/2004 | Hossainy et al. | 427/2.25 |
| 6,872,225 | B1 * | 3/2005 | Rowan et al. | 623/1.15 |
| 2001/0007083 | A1 | 7/2001 | Roorda | |
| 2001/0029660 | A1 | 10/2001 | Johnson | |
| 2001/0032014 | A1 | 10/2001 | Yang et al. | |
| 2001/0034363 | A1 | 10/2001 | Li et al. | |
| 2001/0037145 | A1 | 11/2001 | Guruwaiya et al. | |
| 2002/0041899 | A1 * | 4/2002 | Chudzik et al. | 424/487 |
| 2002/0111590 | A1 | 8/2002 | Davila et al. | 604/265 |
| 2004/0102758 | A1 | 5/2004 | Davila et al. | 604/500 |

FOREIGN PATENT DOCUMENTS

| | | |
|---|---|---|
| EP | 540290 A2 | 10/1992 |
| EP | 0 568 310 A | 11/1993 |
| EP | 604 022 A1 | 6/1994 |
| EP | 621 015 A1 | 10/1994 |
| EP | 623 354 A1 | 11/1994 |
| EP | 734698 A2 | 3/1996 |
| EP | 0 712 615 | 5/1996 |
| EP | 0 716 836 | 6/1996 |
| EP | 716 836 A1 | 6/1996 |
| EP | 800801 A1 | 8/1996 |
| EP | 734 721 A2 | 10/1996 |
| EP | 0 761 251 | 3/1997 |
| EP | 830853 A1 | 7/1997 |
| EP | 0 850 651 | 7/1998 |
| EP | 0 938 878 | 9/1999 |
| EP | 0 938 878 A2 | 9/1999 |
| EP | 0 938 878 A3 | 9/1999 |
| EP | 0 950 386 A2 | 10/1999 |
| FR | 0 566 807 A1 | 4/1992 |
| GB | 0 662 307 A2 | 12/1951 |
| GB | 1 205 743 | 9/1970 |
| WO | WO91/12779 A1 | 9/1991 |
| WO | WO92/15286 A1 | 9/1992 |
| WO | WO94/01056 A1 | 1/1994 |
| WO | WO94/21308 A1 | 9/1994 |
| WO | WO94/21309 A1 | 9/1994 |
| WO | WO94/24961 A1 | 11/1994 |
| WO | WO96/00272 A1 | 1/1996 |
| WO | WO96/26689 B1 | 9/1996 |
| WO | WO96/32907 | 10/1996 |
| WO | WO96/34580 | 11/1996 |
| WO | WO97/25000 A1 | 7/1997 |
| WO | WO97/33534 A1 | 9/1997 |
| WO | WO98/19628 | 5/1998 |
| WO | WO98/23228 | 6/1998 |
| WO | 98/33443 A1 | 8/1998 |
| WO | WO98/34669 | 8/1998 |
| WO | WO98/36784 A | 8/1998 |
| WO | WO98/47447 A1 | 10/1998 |
| WO | WO98/56312 A1 | 12/1998 |
| WO | WO 00/21584 A | 4/2000 |
| WO | WO 00/27445 A | 5/2000 |
| WO | WO 00/32255 A | 6/2000 |
| WO | WO 01/87342 A2 | 11/2001 |
| WO | 02/26139 A1 | 4/2002 |
| WO | WO 02/26281 A1 | 4/2002 |
| WO | 03/000308 A1 | 1/2003 |
| WO | WO 03/015664 A1 | 2/2003 |
| WO | WO 03/057218 A1 | 7/2003 |

OTHER PUBLICATIONS

European Search Report, dated Mar. 1, 2004, for European Appln. No. EP 03 07 8948.

European Search Report dated Sep. 22, 2003 for corresponding Appln. No. EP 03 25 2350.

European Examination Report dated May 12, 2006, for corresponding Appln. No. 05253631.5-2107.

Ajroldi, G. et al., "Fluoroelastomers-dependence of relaxation phenomena on composition," POLYMER, 1989, 30, 2180-2187.

Berk, B. C. et al., "Heparins and Glucocorticoids Inhibit Restenosis," J. Am. Coll. Cardiol., 1991, 17, 111B-117B.

Brehm, B. R. et al., "Beta-blockers of the third generation inhibit endothelin-l liberation, mRNA production and proliferation of human coronary smooth muscle and endothelial cells," J Cardiovasc Pharmacol, Nov. 2000, 36(5 Suppl l), S401-S403.

Campbell, G. R. and Campbell, J. H., "Phenotypic Modulation of Smooth Muscle Cells in Primary Culture," In: *Vascular Smooth Muscle in Culture*, vol. 1, Ch. 4, Boca Raton, FL: CRC, 1987, pp. 39-55.

Campbell, G. R., et al., "Smooth muscle phenotypic changes in arterial wall homeostasis: implications for the pathogenesis of atherosclerosis," Exp. Mol. Pathol., Apr. 1985, 42(2), 139-162.

Carrera, C. J. et al., "Potent toxicity of 2-chlorodeoxyadenosine toward human monocytes in vitro and in vivo. A novel approach to immunosuppressive therapy," J. Clin. Invest, 1990 86(5), 1480-1488.

Carson, D. A. et al., "DNA strand breaks, NAD metabolism, and programmed cell death," Exp Cell Res, Jun. 1986, 164(2), 273-281.

Carson, D. A. et al., "Genetic analysis of deoxyadenosine toxicity in dividing human lymphoblasts," Adv Exp Med Biol, 1986, 195 Pt B, 207-211.

Carson, D. A. et al., "Lymphocyte dysfunction after DNA damage by toxic oxygen species. A model of immunodeficiency," J Exp Med., Mar. 1, 1986; 163(3), 746-751.

Carson, D. A. et al., "Metabolism to methionine and growth stimulation by 5π-methylthioadenosine and 5π-methylthioinosine in mammalian cells," Biochem Biophys Res Commun, Apr. 29, 1983 112(2), 391-397.

Carson, D. A. et al., "Specific toxicity of 2-chlorodeoxyadenosine toward resting and proliferating human lymphocytes," Blood, Oct. 1983 62(4), 737-743.

Chang, M. W. et al., "Adenovirus-mediated Over-expression of the Cyclin/Cyclin-dependent," J. Clin. Invest., 1995, 96, 2260-2268.

Clowes, A. W. et al., "Kinetics of cellular proliferation after arterial injury. II. Inhibition of smooth muscle growth by heparin," Lab. Invest., 1985, 52(6), 611-616.

Clowes, A. W. et al., "Kinetics of cellular proliferation after arterial injury. IV. Heparin inhibits rat smooth muscle mitogenesis and migration," Circ. Res., 1986, 58(6), 839-845.

Clowes, A. W. et al., "Significance of quiescent smooth muscle migration in the injured rat carotid artery," Circ Res. 1985, 56(1), 139-145.

Clowes, A. W., "Suppression by heparin of smooth muscle cell proliferation in injured arteries," Nature, 1977, 265(5595), 625-626.

Colburn, M. D. et al., "Dose responsive suppression of myointimal hyperplasia by dexamethasone," J. Vasc. Surg., 1992, 15, 510-518.

Currier, J. W. et al. "Colchicine Inhibits Restenosis After Iliac Angioplasty in the Atherosclerotic Rabbit," Supplement to Circulation. Abstracts From the 62nd Scientific Sessions., 1989, 80(4), Abstract No. 0263.

Edelman, E. R. et al., "Pathobiologic responses to stenting," Am J. Cardiol. 1998, 81(7A), 4E-6E.

Farb, A. et al., "Vascular smooth muscle cell cytotoxicity and sustained inhibition of neointimal formation by fibroblast growth factor 2-saporin fusion protein," Circ. Res., 1997, 80, 542-550.

Ferns, G. A. A. et al., "Inhibition of Neointimal Smooth Muscle Accumulation After Angioplasty by an Antiboby to PDGF," Science, 1991, 253, 1129-1132.

Fischman, D. L. et al., "A Randomized Comparison of Coronary-Stent Placement and Balloon Angioplasty in the Treatment of Coronary Artery Disease," N. Eng. J. Med., Aug. 25,1994 331(8), 496-501.

Franklin, S. M. et al., "Pharmacologic prevention of restenosis after coronary angioplasty: review of the randomized clinical trials," Coron Artery Dis. Mar. 1993, 4(3), 232-242.

Fukuyama, J. et al., "Tranilast suppresses the vascular intimal hyperplasia after balloon injury in rabbits fed on a high-cholesterol diet," Eur. J. Pharmacol., 1996, 318, 327-332.

Guyton, J. R. et al., "Inhibition of rat arterial smooth muscle cell proliferation by heparin. In vivo studies with anticoagulant and nonanticoagulant heparin," Circ. Res., 1980, 46, 625-634.

Hanson, S. R. et al., "Interruption of acute platelet-dependent thrombosis by the synthetic antithrombin D-phenylalanyl-L-prolyl-L-arginyl chloromethyl ketone," Proc. Natl. Acad. Sci. USA, 1998, 85, 3184-3188.

Hansson, G. K. et al., "Interferon-γ Inhibits Arterial Stenosis After Injury," Circ., 1991, 84, 1266-1272.

Jonasson, J. et al., "Cyclosporin A inhibits smooth muscle proliferation in the vascular response to injury," Proc. Natl., Acad. Sci., 1988, 85, 2303-2306.

Lang, R. J. et al., "Effects of 2,3-butanedione monoxime on whole-cell CA2+ channel currents in single cells of the guinea-pig taenia caeci," J Physiol. Feb. 1991, 433, 1-24.

Lang, R. J. et al., "Effects of okadaic acid and ATP gamma S on cell length and Ca(2+)-channel currents recorded in single smooth muscle cells of the guinea-pig taenia caeci., ", Br. J. Pharmacol., Oct. 1991, 104(2), 331-336.

Liu, M. W. et al., "Trapidil in Preventing Restenosis After Balloon Angioplasty in the Atherosclerotic Rabbit," Circ., 1990, 81, 1089-1093.

Lundergan, C. F. et al., "Peptide Inhibition of Myointimal Proliferation by Agiopeptin, a Somatostatin Analogue," JACC., 1991, 17(6), 132B-136B.

Majesky, M. W. et al., "Heparin regulates smooth muscle S phase entry in the injured rat carotid artery," Circ. Res., 1987, 61, 296-300.

Mak, K-H. et al., "Clinical trials to prevent restenosis after percutaneous coronary revascularization," Ann N Y Acad Sci., Apr. 15, 1997 811, 255-84; discussion 284-8. Review.

Marx, S. O. et al., "Rapamycin-FKBP Inhibits Cell Cycle Regulators of Proliferation in Vascular Smooth Muscle Cells," Circ. Res., 1995, 76, 412-417.

Mintz, G. S. et al., "Arterial remodeling after coronary angioplasty: a serial intravascular ultrasound study," Circulation. Jul. 1, 1996, 94(1), 35-43.

Mintz, G.S. et al., "Axial plaque redistribution as a mechanism of percutaneous transluminal coronary angioplasty," Am J Cardiol, Feb. 15, 1996, 77(5), 427-430.

Mintz, G. S. et al., "Intravascular Ultrasound Assessment of the Mechanisms and Predictors of Restenosis Following Coronary Angioplasty," J Invasive Cardiol., Jan. 1996, 8(1), 1-14.

Mintz, G. S. et al., "Intravascular ultrasound findings after excimer laser coronary angioplasty," Cathet Cardiovasc Diagn. Feb. 1996, 37(2), 113-118.

Mintz, G. S. et al., "Intravascular ultrasound predictors of restenosis after percutaneous transcatheter coronary revascularization," J Am Coll Cardiol, Jun. 1996, 27(7), 1678-1687.

Mintz, G. S. et al., "Intravascular ultrasound to discern device-specific effects and mechanisms of restenosis," Am J Cardiol. Aug. 14, 1996, 78(3A), 18-22.

Mintz, G. S. et al., "Limitations of angioplasty in the assessment of plaque distribution in coronary artery disease: a systematic study of target lesion eccentricity in 1446 lesions," Circulation. Mar. 1, 1996, 93(5), 924-931.

*Modern Fluoropolymers*, (J. Scheirs, ed.), John Wiley & Sons, New York, 1997, pp. 77-87.

Nemecek, G. M. et al., "Terbinafine Inhibits the Mitogenic Response to Platelet-Derived Growth Factor *in Vivo* and Neoinimal Proliferation *in Vitro*, " J. Pharmacol. Exp. Thera., 1989, 248, 1167-1174.

Okada, T. et al., "Localized Release of Perivascular Heparin Inhibits Intimal Proliferation after Endothelial Injury without Systemic Anticoagulation," Neurosurgery, 1989, 25, 892-898.

Popma, J. J. et al, "Atherectomy of right coronary ostial stenoses: initial and long-term results, technical features and histologic findings," Am J Cardiol., Feb. 15, 1991; 67(5), 431-433.

Popma, J.J. et al., "Adjuncts to thrombolysis for myocardial reperfusion," Ann Intern Med., Jul. 1, 1991, 115(1), 34-44.

Popma, J. J. et al., "Clinical trials of restenosis after coronary angioplasty," Circulation, Sep. 1991, 84(3), 1462-1436.

Popma, J. J. et al., "Clinical, angiographic and procedural correlates of quantitative coronary dimensions after directional coronary atherectomy," J Am Coll Cardiol., Nov. 1, 1991, 18(5), 1183-1189.

Powell, J. S. et al., "Inhibitors of Angiotensin-Converting Enzyme Prevent Myointimal Proliferation After Vascular Injury," Science, 1989, 245, 186-188.

Serruys, P. W. et al., "A comparison of balloon-expandable-stent implantation with ballloon angioplasty in patients with coronary artery disease," N Engl J Med, Aug. 25, 1994; 331(8), 489-495.

Serruys, P. W. et al., "Evaluation of ketanserin in the prevention of restenosis after percutaneous transluminal coronary angioplasty. A multicenter randomized double-blind placebo-controlled trial," Circulation. Oct. 1993; 88(4 Pt 1), 1588-1601.

Serruys, P. W. et al., "Heparin-coated Palmaz-Schatz stents in human coronary arteries. Early outcome of the Benestent-II Pilot Study," Circulation, Feb. 1, 1996; 93(3), 412-422.

Serruys, P. W. et al., "Randomized trials of coronary stenting," J Interv Cardiol, Aug. 1994; 7(4), 331.

Serruys, P. W. et al., "Restenosis revisited: insights provided by quantitative coronary angiography," Am Heart J, Nov. 1993; 126(5), 1243-1267.

Serruys, P. W. et al., "The bailout stent. Is a friend in need always a friend indeed?" Circulation, Nov. 1993; 88(5 Pt 1), 2455-2457.

Seto, S. et al., "Mechanism of deoxyadenosine and 2-chlorodeoxyadenosine toxicity to nondividing human lymphocytes," J Clin Invest. Feb. 1985, 75(2), 377-383.

Simons, M. et al., "Antisense c-*myb* oligonucleotides inhibit intimal arterial smooth muscle cell accumulation *in vivo*, " Nature, 1992, 359, 67-70.

Snow, A. D. et al., "Heparin modulates the compostion of the extracellular matrix domain surrounding arterial smooth muscle cells," Am. J. Pathol., 1990, 137, 313-330.

Sollot, S. J. et al., "Taxol Inhibits Neointimal Smooth Muscle Cell Accumulation after Angioplasty in the Rat," J. Clin. Invest., 1995, 95, 1869-1876.

Tanaka, H. et al., "Sustained activation of vascular cells and leukocytes in the rabbit aorta after balloon injury," Circulation, OCt. 1993; 88(4 Pt 1), 1788-1803.

Tardif, et al., "Probucol and multivitamins in the prevention of restenosis after coronary angioplasty. Multivitamins and Probucol Study Group," N Engl J Med. Aug. 7 1997; 337(6), 365-372.

Teirstein, P.S. et al., "Catheter-based radiotherapy to inhibit restenosis after coronary stenting," N Engl J Med., Jun. 12, 1997; 336(24), 1697-1703.

Weinberger, J. et al., "Intracoronary irradiation: dose response for the prevention of restenosis in swine," Int. J. Rad. Onc. Biol. Phys., 1996, 36, 767-775.

Yokoi, H. et al., "Effectiveness of an antioxidant in preventing restenosis after percutaneous transluminal coronary angioplasty: the Probucol Angioplasty Restenosis Trial," J Am Coll Cardiol., Oct. 1997; 30(4), 855-862.

* cited by examiner

LOCAL DRUG DELIVERY DEVICES AND METHODS FOR MAINTAINING THE DRUG COATINGS THEREON

CROSS REFERENCE TO RELATED APPLICATIONS

This application is a continuation-in-part application of U.S. application Ser. No. 09/850,482 filed May 7, 2001.

BACKGROUND OF THE INVENTION

1. Field of the Invention

The present invention relates to the local administration of drug/drug combinations for the prevention and treatment of vascular disease, and more particularly to intraluminal medical devices for the local delivery of drug/drug combinations for the prevention and treatment of vascular disease caused by injury and methods for maintaining the drug/drug combinations on the intraluminal medical devices. The present invention also relates to medical devices having drugs, agents or compounds affixed thereto to minimize or substantially eliminate a biological organism's reaction to the introduction of the medical device to the organism.

2. Discussion of the Related Art

Many individuals suffer from circulatory disease caused by a progressive blockage of the blood vessels that profuse the heart and other major organs with nutrients. More severe blockage of blood vessels in such individuals often leads to hypertension, ischemic injury, stroke, or myocardial infarction. Atherosclerotic lesions, which limit or obstruct coronary blood flow, are the major cause of ischemic heart disease. Percutaneous transluminal coronary angioplasty is a medical procedure whose purpose is to increase blood flow through an artery. Percutaneous transluminal coronary angioplasty is the predominant treatment for coronary vessel stenosis. The increasing use of this procedure is attributable to its relatively high success rate and its minimal invasiveness compared with coronary bypass surgery. A limitation associated with percutaneous transluminal coronary angioplasty is the abrupt closure of the vessel which may occur immediately after the procedure and restenosis which occurs gradually following the procedure. Additionally, restenosis is a chronic problem in patients who have undergone saphenous vein bypass grafting. The mechanism of acute occlusion appears to involve several factors and may result from vascular recoil with resultant closure of the artery and/or deposition of blood platelets and fibrin along the damaged length of the newly opened blood vessel.

Restenosis after percutaneous transluminal coronary angioplasty is a more gradual process initiated by vascular injury. Multiple processes, including thrombosis, inflammation, growth factor and cytokine release, cell proliferation, cell migration and extracellular matrix synthesis each contribute to the restenotic process.

While the exact mechanism of restenosis is not completely understood, the general aspects of the restenosis process have been identified. In the normal arterial wall, smooth muscle cells proliferate at a low rate, approximately less than 0.1 percent per day. Smooth muscle cells in the vessel walls exist in a contractile phenotype characterized by eighty to ninety percent of the cell cytoplasmic volume occupied with the contractile apparatus. Endoplasmic reticulum, Golgi, and free ribosomes are few and are located in the perinuclear region. Extracellular matrix surrounds the smooth muscle cells and is rich in heparin-like glycosylaminoglycans which are believed to be responsible for maintaining smooth muscle cells in the contractile phenotypic state (Campbell and Campbell, 1985).

Upon pressure expansion of an intracoronary balloon catheter during angioplasty, smooth muscle cells within the vessel wall become injured, initiating a thrombotic and inflammatory response. Cell derived growth factors such as platelet derived growth factor, basic fibroblast growth factor, epidermal growth factor, thrombin, etc., released from platelets, invading macrophages and/or leukocytes, or directly from the smooth muscle cells provoke a proliferative and migratory response in medial smooth muscle cells. These cells undergo a change from the contractile phenotype to a synthetic phenotype characterized by only a few contractile filament bundles, extensive rough endoplasmic reticulum, Golgi and free ribosomes. Proliferation/migration usually begins within one to two days post-injury and peaks several days thereafter (Campbell and Campbell, 1987; Clowes and Schwartz, 1985).

Daughter cells migrate to the intimal layer of arterial smooth muscle and continue to proliferate and secrete significant amounts of extracellular matrix proteins. Proliferation, migration and extracellular matrix synthesis continue until the damaged endothelial layer is repaired at which time proliferation slows within the intima, usually within seven to fourteen days post-injury. The newly formed tissue is called neointima. The further vascular narrowing that occurs over the next three to six months is due primarily to negative or constrictive remodeling.

Simultaneous with local proliferation and migration, inflammatory cells adhere to the site of vascular injury. Within three to seven days post-injury, inflammatory cells have migrated to the deeper layers of the vessel wall. In animal models employing either balloon injury or stent implantation, inflammatory cells may persist at the site of vascular injury for at least thirty days (Tanaka et al., 1993; Edelman et al., 1998). Inflammatory cells therefore are present and may contribute to both the acute and chronic phases of restenosis.

Numerous agents have been examined for presumed anti-proliferative actions in restenosis and have shown some activity in experimental animal models. Some of the agents which have been shown to successfully reduce the extent of intimal hyperplasia in animal models include: heparin and heparin fragments (Clowes, A. W. and Karnovsky M., Nature 265: 25–26, 1977; Guyton, J. R. et al., Circ. Res., 46: 625–634,1980; Clowes, A. W. and Clowes, M. M., Lab. Invest. 52: 611–616, 1985; Clowes, A. W. and Clowes, M. M., Circ. Res. 58: 839–845, 1986; Majesky et al., Circ. Res. 61: 296–300, 1987; Snow et al., Am. J. Pathol. 137: 313–330, 1990; Okada, T. et al., Neurosurgery 25: 92–98, 1989), colchicine (Currier, J. W. et al., Circ. 80: 11–66, 1989), taxol (Sollot, S. J. et al., J. Clin. Invest. 95: 1869–1876, 1995), angiotensin converting enzyme (ACE) inhibitors (Powell, J. S. et al., Science, 245: 186–188, 1989), angiopeptin (Lundergan, C. F. et al. Am. J. Cardiol. 17(Suppl. B):132B–136B, 1991), cyclosporin A (Jonasson, L. et al., Proc. Natl., Acad. Sci., 85: 2303, 1988), goat-anti-rabbit PDGF antibody (Ferns, G. A. A., et al., Science 253: 1129–1132, 1991), terbinafine (Nemecek, G. M. et al., J. Pharmacol. Exp. Thera. 248: 1167–1174, 1989), trapidil (Liu, M. W. et al., Circ. 81: 1089–1093, 1990), tranilast (Fukuyama, J. et al., Eur. J. Pharmacol. 318: 327–332, 1996), interferongamma (Hansson, G. K. and Holm, J., Circ. 84: 1266–1272, 1991), rapamycin (Marx, S. O. et al., Circ. Res. 76: 412–417, 1995), steroids (Colburn, M. D. et al., J. Vasc. Surg. 15: 510–518, 1992), see also Berk, B. C. et al., J. Am. Coll. Cardiol. 17: 111B–117B , 1991), ionizing radiation (Weinberger, J. et al., Int. J. Rad. Onc. Biol. Phys. 36: 767–775, 1996), fusion toxins (Farb, A. et al., Circ. Res. 80: 542–550, 1997) antisense oligonucleotides (Simons, M. et al., Nature 359: 67–70,1992) and gene vectors (Chang, M. W. et al., J. Clin. Invest. 96: 2260–2268, 1995). Antiproliferative action on smooth muscle cells in vitro has been demonstrated for many of these agents, including heparin and heparin conjugates, taxol, tranilast, colchicine, ACE inhibitors, fusion toxins, antisense oligonucleotides, rapamycin and ionizing radiation. Thus, agents with diverse mechanisms of smooth muscle cell inhibition may have therapeutic utility in reducing intimal hyperplasia.

However, in contrast to animal models, attempts in human angioplasty patients to prevent restenosis by systemic pharmacologic means have thus far been unsuccessful. Neither aspirin-dipyridamole, ticlopidine, anti-coagulant therapy (acute heparin, chronic warfarin, hirudin or hirulog), thromboxane receptor antagonism nor steroids have been effective in preventing restenosis, although platelet inhibitors have been effective in preventing acute reocclusion after angioplasty (Mak and Topol, 1997; Lang et al., 1991; Popma et al., 1991). The platelet GP IIb/IIIa receptor, antagonist, Reopro is still under study but has not shown promising results for the reduction in restenosis following angioplasty and stenting. Other agents, which have also been unsuccessful in the prevention of restenosis, include the calcium channel antagonists, prostacyclin mimetics, angiotensin converting enzyme inhibitors, serotonin receptor antagonists, and anti-proliferative agents. These agents must be given systemically, however, and attainment of a therapeutically effective dose may not be possible; anti-proliferative (or anti-restenosis) concentrations may exceed the known toxic concentrations of these agents so that levels sufficient to produce smooth muscle inhibition may not be reached (Mak and Topol, 1997; Lang et al., 1991; Popma et al., 1991).

Additional clinical trials in which the effectiveness for preventing restenosis utilizing dietary fish oil supplements or cholesterol lowering agents has been examined showing either conflicting or negative results so that no pharmacological agents are as yet clinically available to prevent post-angioplasty restenosis (Mak and Topol, 1997; Franklin and Faxon, 1993: Serruys, P. W. et al., 1993). Recent observations suggest that the antilipid/antioxident agent, probucol may be useful in preventing restenosis but this work requires confirmation (Tardif et al., 1997; Yokoi, et al., 1997). Probucol is presently not approved for use in the United States and a thirty-day pretreatment period would preclude its use in emergency angioplasty. Additionally, the application of ionizing radiation has shown significant promise in reducing or preventing restenosis after angioplasty in patients with stents (Teirstein et al., 1997). Currently, however, the most effective treatments for restenosis are repeat angioplasty, atherectomy or coronary artery bypass grafting, because no therapeutic agents currently have Food and Drug Administration approval for use for the prevention of post-angioplasty restenosis.

Unlike systemic pharmacologic therapy, stents have proven useful in significantly reducing restenosis. Typically, stents are balloon-expandable slotted metal tubes (usually, but not limited to, stainless steel), which, when expanded within the lumen of an angioplastied coronary artery, provide structural support through rigid scaffolding to the arterial wall. This support is helpful in maintaining vessel lumen patency. In two randomized clinical trials, stents increased angiographic success after percutaneous transluminal coronary angioplasty, by increasing minimal lumen diameter and reducing, but not eliminating, the incidence of restenosis at six months (Serruys et al., 1994; Fischman et al., 1994).

Additionally, the heparin coating of stents appears to have the added benefit of producing a reduction in sub-acute thrombosis after stent implantation (Serruys et al., 1996). Thus, sustained mechanical expansion of a stenosed coronary artery with a stent has been shown to provide some measure of restenosis prevention, and the coating of stents with heparin has demonstrated both the feasibility and the clinical usefulness of delivering drugs locally, at the site of injured tissue.

As stated above, the use of heparin coated stents demonstrates the feasibility and clinical usefulness of local drug delivery; however, the manner in which the particular drug or drug combination is affixed to the local delivery device will play a role in the efficacy of this type of treatment. For example, the processes and materials utilized to affix the drug/drug combinations to the local delivery device should not interfere with the operations of the drug/drug combinations. In addition, the processes and materials utilized should be biocompatible and maintain the drug/drug combinations on the local device through delivery and over a given period of time. For example, removal of the drug/drug combination during delivery of the local delivery device may potentially cause failure of the device.

Accordingly, there exists a need for drug/drug combinations and associated local delivery devices for the prevention and treatment of vascular injury causing intimal thickening which is either biologically induced, for example atherosclerosis, or mechanically induced, for example, through percutaneous transluminal coronary angioplasty. In addition, there exists a need for maintaining the drug/drug combinations on the local delivery device through delivery and positioning as well as ensuring that the drug/drug combination is released in therapeutic dosages over a given period of time.

SUMMARY OF THE INVENTION

The drug/drug combinations and associated local delivery devices of the present invention provide a means for overcoming the difficulties associated with the methods and devices currently in use, as briefly described above. In addition, the methods for maintaining the drug/drug combinations on the local delivery device ensure that the drug/drug combinations reach the target site.

In accordance with one aspect, the present invention is directed to a local drug delivery apparatus. The local drug delivery apparatus comprises a medical device for implantation into a treatment site of a living organism and at least one agent in therapeutic dosages releasable affixed to the medical device for the treatment of reactions by the living organism caused by the medical device or the implantation thereof. The local delivery apparatus also comprises a material for preventing the at least one agent from separating from the medical device prior to implantation of the medical device at the treatment site, the material being affixed to at least one of the medical device or a delivery system for the medical device.

In accordance with another aspect, the present invention is directed to a local drug delivery apparatus. The local drug delivery apparatus comprises a medical device for implantation into a treatment site of a living organism and at least one agent in therapeutic dosages releasably affixed to the medical device for the treatment of reactions by the living organism caused by the medical device or the implantation thereof, the at least one agent being incorporated into a polymeric matrix. The local drug delivery apparatus also comprises a material for preventing the at least one agent from separating from the medical device prior to implantation of the medical device at the treatment site, the material being affixed to at least one of the medical device or a delivery system for the medical device.

In accordance with another aspect, the present invention is directed to a local drug delivery apparatus. The local drug delivery apparatus comprises a medical device for implantation into a treatment site of a living organism and at least one agent in therapeutic dosages releasably affixed to the medical device for the treatment of reactions by the living organism caused by the medical device or the implantation thereof, the at least one agent being incorporated into a polymeric matrix. The local drug delivery apparatus also comprises a material for preventing the polymeric matrix from adhering to itself when parts of the medical device make contact with one another.

In accordance with another aspect, the present invention is directed to a drug delivery device. The drug delivery device comprises a medical device for implantation into a treatment site of a living organism, and therapeutic dosages of one or more anti-proliferatives, one or more anti-inflammatories, one or more anti-coagulants, and one or more immunosuppressants releasably affixed to the medical device for the treatment of reactions by the living organism caused by the medical device or the implantation of the medical device at the treatment site.

In accordance with another aspect, the present invention is directed to a method for maintaining agents on a medical device during implantation into a treatment site of a living organism. The method comprises releasably affixing one or more agents in therapeutic dosages to the medical device, treating one of the medical device or the delivery device with a material for preventing the one or more agents from separating from the medical device during delivery and implantation of the medical device at the treatment site, and loading the medical device into a delivery device.

In accordance with another aspect, the present invention is directed to a method for maintaining agents on a medical device during implantation into a treatment site of a living organism. The method comprises releasably affixing one or more agents in therapeutic dosages to the medical device by incorporating the one or more agents in at least one polymer, treating the medical device with a material for preventing the polymer from adhering to itself when parts of the medical device make contact, and loading the medical device into a delivery device.

In accordance with another aspect, the present invention is directed to a method for maintaining agents on a medical device during implantation into a treatment site of a living organism. The method comprises coating at least a portion of the medical device with a primer layer, coating the primer layer with a first polymer layer including cross-linking moieties, cross-linking the first polymer layer to the primer layer, and releasably affixing one or more agents in therapeutic dosages to the medical device by incorporating the one or more agents in at least one polymer, the polymer being similar in chemical composition to the first polymer.

The local drug delivery devices and methods for maintaining the drug coatings thereon of the present invention utilizes a combination of materials to treat disease, and reactions by living organisms due to the implantation of medical devices for the treatment of disease or other conditions. The local delivery of drugs, agents or compounds generally substantially reduces the potential toxicity of the drugs, agents or compounds when compared to systemic delivery while increasing their efficacy.

Drugs, agents or compounds may be affixed to any number of medical devices to treat various diseases. The drugs, agents or compounds may also be affixed to minimize or substantially eliminate the biological organism's reaction to the introduction of the medical device utilized to treat a separate condition. For example, stents may be introduced to open coronary arteries or other body lumens such as biliary ducts. The introduction of these stents cause a smooth muscle cell proliferation effect as well as inflammation. Accordingly, the stents may be coated with drugs to combat these reactions.

In order to be effective, the drugs, agents or compounds should preferably remain on the medical devices during delivery and implantation. Accordingly, various coating techniques for creating strong bonds between the drugs, agents or compounds may be utilized. In addition, various materials may be utilized as surface modifications to prevent the drugs, agents or compounds from coming off prematurely.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

The drug/drug combinations and delivery devices of the present invention may be utilized to effectively prevent and treat vascular disease, and in particular, vascular disease caused by injury. Various medical treatment devices utilized in the treatment of vascular disease may ultimately induce further complications. For example, balloon angioplasty is a procedure utilized to increase blood flow through an artery and is the predominant treatment for coronary vessel stenosis. However, as stated above, the procedure typically causes a certain degree of damage to the vessel wall, thereby potentially exacerbating the problem at a point later in time. Although other procedures and diseases may cause similar injury, the present invention will be described with respect to the treatment of restenosis and related complications following percutaneous transluminal coronary angioplasty.

While the invention will be described with respect to the treatment of restenosis and related complications following percutaneous transluminal coronary angioplasty, it is important to note that the local delivery of drug/drug combinations may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach. Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bonemorphogenic protein. Similarly other surgical devices, sutures, staples, vertebral disks, bone pins, suture anchors, hemostatic barriers, clamps, screws, plates, clips, vascular implants; tissue adhesives and sealants, tissue scaffolds, various types of dressings, bone substitutes, intraluminal devices, and vascular supports could also provide enhanced patient benefit using this drug-device combination approach. Essentially, any type of medical device may be coated in some fashion with a drug or drug combination which enhances treatment over use of the singular use of the device or pharmaceutical agent.

As stated previously, the implantation of a coronary stent in conjunction with balloon angioplasty is highly effective in treating acute vessel closure and may reduce the risk of restenosis. Intravascular ultrasound studies (Mintz et al., 1996) suggest that coronary stenting effectively prevents vessel constriction and that most of the late luminal loss after stent implantation is due to plaque growth, probably related to neointimal hyperplasia. The late luminal loss after coronary stenting is almost two times higher than that observed after conventional balloon angioplasty. Thus, inasmuch as stents prevent at least a portion of the restenosis process, a combination of drugs, agents or compounds which prevents smooth muscle cell proliferation, reduces inflammation and reduces coagulation or prevents smooth muscle cell proliferation by multiple mechanisms, reduces inflammation and reduces coagulation combined with a stent may provide the most efficacious treatment for post-angioplasty restenosis. The systemic use of drugs, agents or compounds in combination with the local delivery of the same or different drug/drug combinations may also provide a beneficial treatment option.

The local delivery of drug/drug combinations from a stent has the following advantages; namely, the prevention of vessel recoil and remodeling through the scaffolding action of the stent and the prevention of multiple components of neointimal hyperplasia or restenosis as well as a reduction in inflammation and thrombosis. This local administration of drugs, agents or compounds to stented coronary arteries may also have additional therapeutic benefit. For example, higher tissue concentrations of the drugs, agents or compounds can be achieved utilizing local delivery, rather than systemic administration. In addition, reduced systemic toxicity may be achieved utilizing local delivery rather than systemic administration while maintaining higher tissue concentrations. Also in utilizing local delivery from a stent rather than systemic administration, a single procedure may suffice with better patient compliance. An additional benefit of combination drug/agent/compound therapy may be to reduce the dose of each of the therapeutic drugs, agents or compounds, thereby limiting their toxicity, while still achieving a reduction in restenosis, inflammation and thrombosis. Local stent-based therapy is therefore a means of improving the therapeutic ratio (efficacy/toxicity) of anti-restenosis, anti-inflammatory, anti-thrombotic drugs, agents or compounds.

There are a multiplicity of different stents that may be utilized following percutaneous transluminal coronary angioplasty. Although any number of stents may be utilized in accordance with the present invention, for simplicity, one particular stent will be described in exemplary embodiments of the present invention. The skilled artisan will recognize that any number of stents may be utilized in connection with the present invention. In addition, as stated above, other medical devices may be utilized.

A stent is commonly used as a tubular structure left inside the lumen of a duct to relieve an obstruction. Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen.

Figure 1:
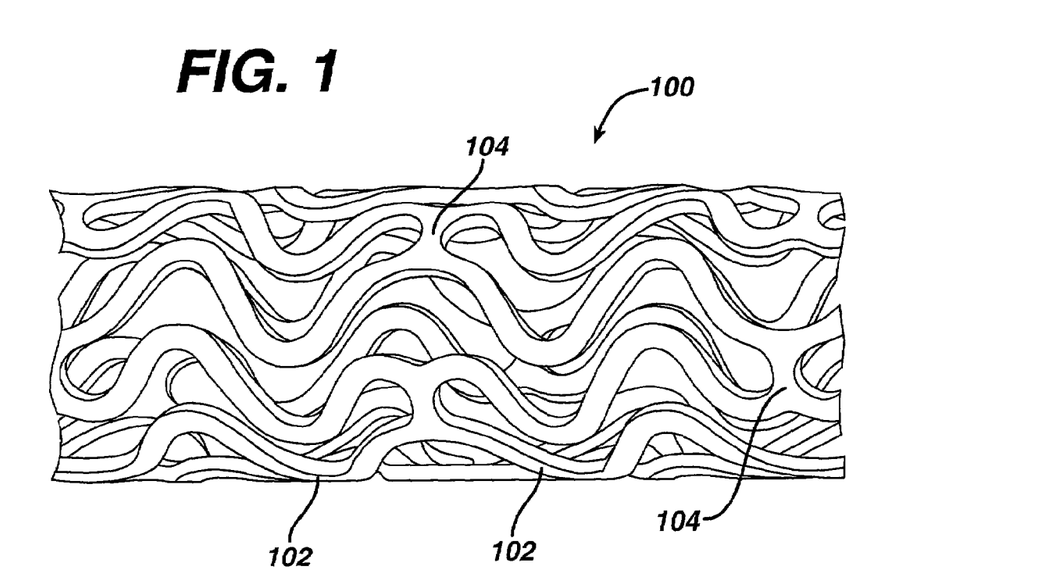
FIG. 1 is a view along the length of a stent (ends not shown) prior to expansion showing the exterior surface of the stent and the characteristic banding pattern.

FIG. 1 illustrates an exemplary stent 100 which may be utilized in accordance with an exemplary embodiment of the present invention. The expandable cylindrical stent 100 comprises a fenestrated structure for placement in a blood vessel, duct or lumen to hold the vessel, duct or lumen open, more particularly for protecting a segment of artery from restenosis after angioplasty. The stent 100 may be expanded circumferentially and maintained in an expanded configuration, that is circumferentially or radially rigid. The stent 100 is axially flexible and when flexed at a band, the stent 100 avoids any externally-protruding component parts.

The stent 100 generally comprises first and second ends with an intermediate section therebetween. The stent 100 has a longitudinal axis and comprises a plurality of longitudinally disposed bands 102, wherein each band 102 defines a generally continuous wave along a line segment parallel to the longitudinal axis. A plurality of circumferentially arranged links 104 maintain the bands 102 in a substantially tubular structure. Essentially, each longitudinally disposed band 102 is connected at a plurality of periodic locations, by a short circumferentially arranged link 104 to an adjacent band 102. The wave associated with each of the bands 102 has approximately the same fundamental spatial frequency in the intermediate section, and the bands 102 are so disposed that the wave associated with them are generally aligned so as to be generally in phase with one another. As illustrated in the figure, each longitudinally arranged band 102 undulates through approximately two cycles before there is a link to an adjacent band 102.

The stent 100 may be fabricated utilizing any number of methods. For example, the stent 100 may be fabricated from a hollow or formed stainless steel tube that may be machined using lasers, electric discharge milling, chemical etching or other means. The stent 100 is inserted into the body and placed at the desired site in an unexpanded form. In one embodiment, expansion may be effected in a blood vessel by a balloon catheter, where the final diameter of the stent 100 is a function of the diameter of the balloon catheter used.

It should be appreciated that a stent 100 in accordance with the present invention may be embodied in a shape-memory material, including, for example, an appropriate alloy of nickel and titanium or stainless steel. In this embodiment after the stent 100 has been formed it may be compressed so as to occupy a space sufficiently small as to permit its insertion in a blood vessel or other tissue by insertion means, wherein the insertion means include a suitable catheter, or flexible rod. On emerging from the catheter, the stent 100 may be configured to expand into the desired configuration where the expansion is automatic or triggered by a change in pressure, temperature or electrical stimulation.

Figure 2:
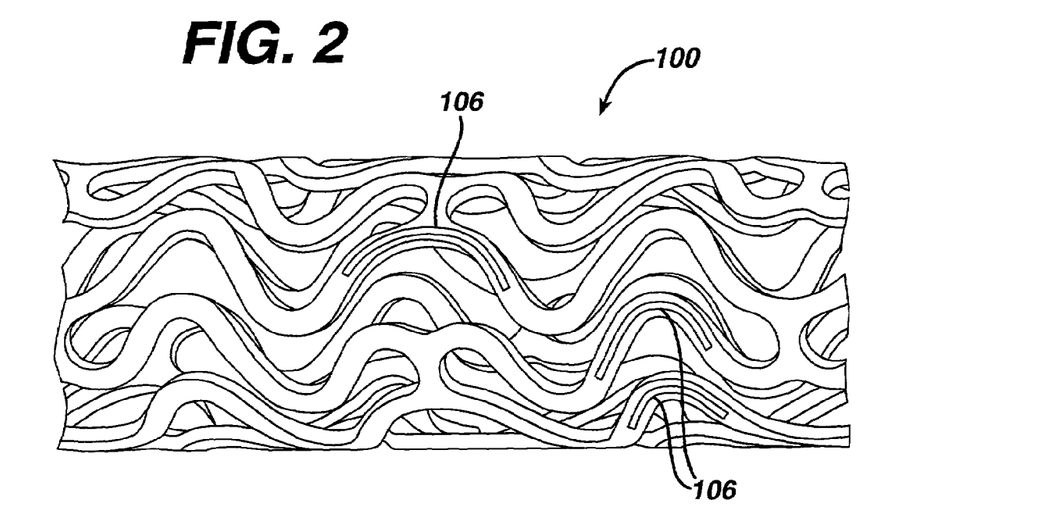
FIG. 2 is a perspective view of the stent of FIG. 1 having reservoirs in accordance with the present invention.

FIG. 2 illustrates an exemplary embodiment of the present invention utilizing the stent 100 illustrated in FIG. 1. As illustrated, the stent 100 may be modified to comprise one or more reservoirs 106. Each of the reservoirs 106 may be opened or closed as desired. These reservoirs 106 may be specifically designed to hold the drug/drug combinations to be delivered. Regardless of the design of the stent 100, it is preferable to have the drug/drug combination dosage applied with enough specificity and a sufficient concentration to provide an effective dosage in the lesion area. In this regard, the reservoir size in the bands 102 is preferably sized to adequately apply the drug/drug combination dosage at the desired location and in the desired amount.

In an alternate exemplary embodiment, the entire inner and outer surface of the stent 100 may be coated with drug/drug combinations in therapeutic dosage amounts. A detailed description of a drug for treating restenosis, as well as exemplary coating techniques, is described below. It is, however, important to note that the coating techniques may vary depending on the drug/drug combinations. Also, the coating techniques may vary depending on the material comprising the stent or other intraluminal medical device.

Rapamycin is a macroyclic triene antibiotic produced by streptomyces hygroscopicus as disclosed in U.S. Pat. No. 3,929,992. It has been found that rapamycin among other things inhibits the proliferation of vascular smooth muscle cells in vivo. Accordingly, rapamycin may be utilized in treating intimal smooth muscle cell hyperplasia, restenosis, and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endothelialization of the vessel walls.

Rapamycin reduces vascular hyperplasia by antagonizing smooth muscle proliferation in response to mitogenic signals that are released during an angioplasty induced injury. Inhibition of growth factor and cytokine mediated smooth muscle proliferation at the late GI phase of the cell cycle is believed to be the dominant mechanism of action of rapamycin. However, rapamycin is also known to prevent T-cell proliferation and differentiation when administered systemically. This is the basis for its immunosuppresive activity and its ability to prevent graft rejection.

As used herein, rapamycin includes rapamycin and all analogs, derivatives and congeners that find FKBP12 and possesses the same pharmacologic properties as rapamycin.

Although the anti-proliferative effects of rapamycin may be achieved through systemic use, superior results may be achieved through the local delivery of the compound. Essentially, rapamycin works in the tissues, which are in proximity to the compound, and has diminished effect as the distance from the delivery device increases. In order to take advantage of this effect, one would want the rapamycin in direct contact with the lumen walls. Accordingly, in a preferred embodiment, the rapamycin is incorporated onto the surface of the stent or portions thereof. Essentially, the rapamycin is preferably incorporated into the stent 100, illustrated in FIG. 1, where the stent 100 makes contact with the lumen wall.

Rapamycin may be incorporated into or affixed to the stent in a number of ways. In the exemplary embodiment, the rapamycin is directly incorporated into a polymeric matrix and sprayed onto the outer surface of the stent. The rapamycin elutes from the polymeric matrix over time and enters the surrounding tissue. The rapamycin preferably remains on the stent for at least three days up to approximately six months, and more preferably between seven and thirty days.

Any number of non-erodible polymers may be utilized in conjunction with the rapamycin. In the exemplary embodiment, the polymeric matrix comprises two layers. The base layer comprises a solution of ethylene-co-vinylacetate and polybutylmethacrylate. The rapamycin is incorporated into this base layer. The outer layer comprises only polybutylmethacrylate and acts as a diffusion barrier to prevent the rapamycin from eluting too quickly. The thickness of the outer layer or top coat determines the rate at which the rapamycin elutes from the matrix. Essentially, the rapamycin elutes from the matrix by diffusion through the polymer molecules. Polymers are permeable, thereby allowing solids, liquids and gases to escape therefrom. The total thickness of the polymeric matrix is in the range from about 1 micron to about 20 microns or greater.

The ethylene-co-vinylacetate, polybutylmethacrylate and rapamycin solution may be incorporated into or onto the stent in a number of ways. For example, the solution may be sprayed onto the stent or the stent may be dipped into the solution. Other methods include spin coating and RF-plasma polymerization. In one exemplary embodiment, the solution is sprayed onto the stent and then allowed to dry. In another exemplary embodiment, the solution may be electrically charged to one polarity and the stent electrically changed to the opposite polarity. In this manner, the solution and stent will be attracted to one another. In using this type of spraying process, waste may be reduced and more precise control over the thickness of the coat may be achieved.

Since rapamycin acts by entering the surrounding tissue, it s preferably only affixed to the surface of the stent making contact with one tissue. Typically, only the outer surface of the stent makes contact with the tissue. Accordingly, in a preferred embodiment, only the outer surface of the stent is coated with rapamycin.

The circulatory system, under normal conditions, has to be self-sealing, otherwise continued blood loss from an injury would be life threatening. Typically, all but the most catastrophic bleeding is rapidly stopped though a process known as hemostasis. Hemostasis occurs through a progression of steps. At high rates of flow, hemostasis is a combination of events involving platelet aggregation and fibrin formation. Platelet aggregation leads to a reduction in the blood flow due to the formation of a cellular plug while a cascade of biochemical steps leads to the formation of a fibrin clot.

Fibrin clots, as stated above, form in response to injury. There are certain circumstances where blood clotting or clotting in a specific area may pose a health risk. For example, during percutaneous transluminal coronary angioplasty, the endothelial cells of the arterial walls are typically injured, thereby exposing the sub-endothelial cells. Platelets adhere to these exposed cells. The aggregating platelets and the damaged tissue initiate further biochemical process resulting in blood coagulation. Platelet and fibrin blood clots may prevent the normal flow of blood to critical areas. Accordingly, there is a need to control blood clotting in various medical procedures. Compounds that do not allow blood to clot are called anti-coagulants. Essentially, an anticoagulant is an inhibitor of thrombin formation or function. These compounds include drugs such as heparin and hirudin. As used herein, heparin includes all direct or indirect inhibitors of thrombin or Factor Xa.

In addition to being an effective anti-coagulant, heparin has also been demonstrated to inhibit smooth muscle cell growth in vivo. Thus, heparin may be effectively utilized in conjunction with rapamycin in the treatment of vascular disease. Essentially, the combination of rapamycin and heparin may inhibit smooth muscle cell growth via two different mechanisms in addition to the heparin acting as an anti-coagulant.

Because of its multifunctional chemistry, heparin may be immobilized or affixed to a stent in a number of ways. For example, heparin may be immobilized onto a variety of surfaces by various methods, including the photolink methods set forth in U.S. Pat. Nos. 3,959,078 and 4,722,906 to Guire et al. and U.S. Pat. Nos. 5,229,172; 5,308,641; 5,350,800 and 5,415,938 to Cahalan et al. Heparinized surfaces have also been achieved by controlled release from a polymer matrix, for example, silicone rubber, as set forth in U.S. Pat. Nos. 5,837,313; 6,099,562 and 6,120,536 to Ding et al.

In one exemplary embodiment, heparin may be immobilized onto the stent as briefly described below. The surface onto which the heparin is to be affixed is cleaned with ammonium peroxidisulfate. Once cleaned, alternating layers of polyethylenimine and dextran sulfate are deposited thereon. Preferably, four layers of the polyethylenimine and dextran sulfate are deposited with a final layer of polyethylenimine. Aldehyde-end terminated heparin is then immobilized to this final layer and stabilized with sodium cyanoborohydride. This process is set forth in U.S. Pat. Nos. 4,613,665; 4,810,784 to Larm and 5,049,403 to Larm et al.

Unlike rapamycin, heparin acts on circulating proteins in the blood and heparin need only make contact with blood to be effective. Accordingly, if used in conjunction with a medical device, such as a stent, it would preferably be only on the side that comes into contact with the blood. For example, if heparin were to be administered via a stent, it would only have to be on the inner surface of the stent to be effective.

Figure 3:
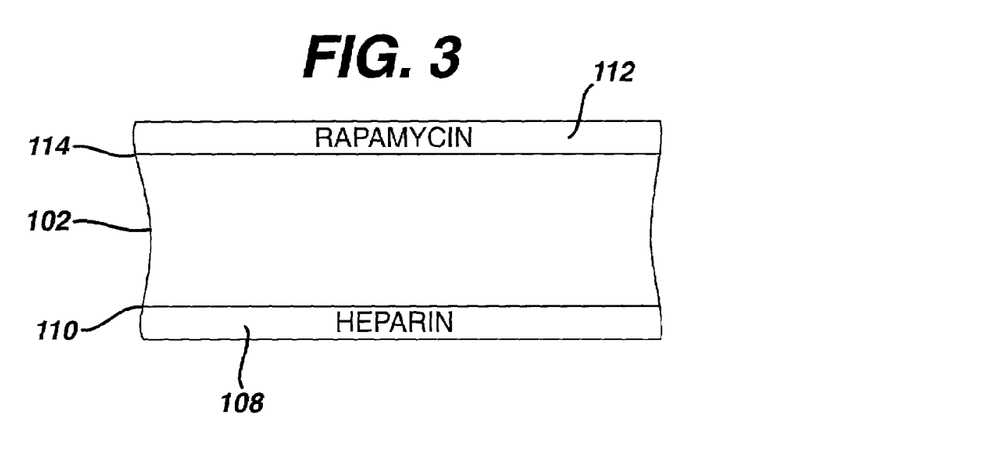
FIG. 3 is a cross-sectional view of a band of the stent of FIG. 1 having drug coatings thereon in accordance with a first exemplary embodiment of the invention.

In an exemplary embodiment of the invention, a stent may be utilized in combination with rapamycin and heparin to treat vascular disease. In this exemplary embodiment, the heparin is immobilized to the inner surface of the stent so that it is in contact with the blood and the rapamycin is immobilized to the outer surface of the stent so that it is in contact with the surrounding tissue. FIG. 3 illustrates a cross-section of a band 102 of the stent 100 illustrated in FIG. 1. As illustrated, the band 102 is coated with heparin 108 on its inner surface 110 and with rapamycin 112 on its outer surface 114.

Figure 4:
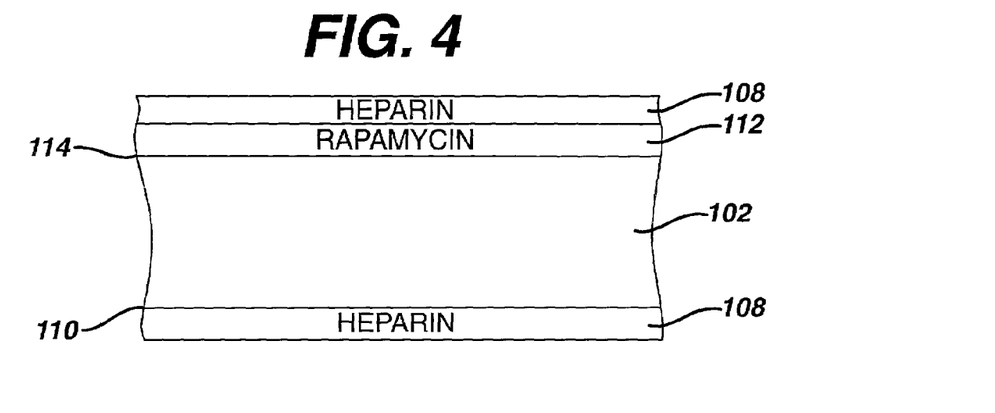
FIG. 4 is a cross-sectional view of a band of the stent of FIG. 1 having drug coatings thereon in accordance with a second exemplary embodiment of the invention.

In an alternate exemplary embodiment, the stent may comprise a heparin layer immobilized on its inner surface, and rapamycin and heparin on its outer surface. Utilizing current coating techniques, heparin tends to form a stronger bond with the surface it is immobilized to then does rapamycin. Accordingly, it may be possible to first immobilize the rapamycin to the outer surface of the stent and then immobilize a layer of heparin to the rapamycin layer. In this embodiment, the rapamycin may be more securely affixed to the stent while still effectively eluting from its polymeric matrix, through the heparin and into the surrounding tissue. FIG. 4 illustrates a cross-section of a band 102 of the stent 100 illustrated in FIG. 1. As illustrated, the band 102 is coated with heparin 108 on its inner surface 110 and with rapamycin 112 and heparin 108 on its outer surface 114.

Figure 5:
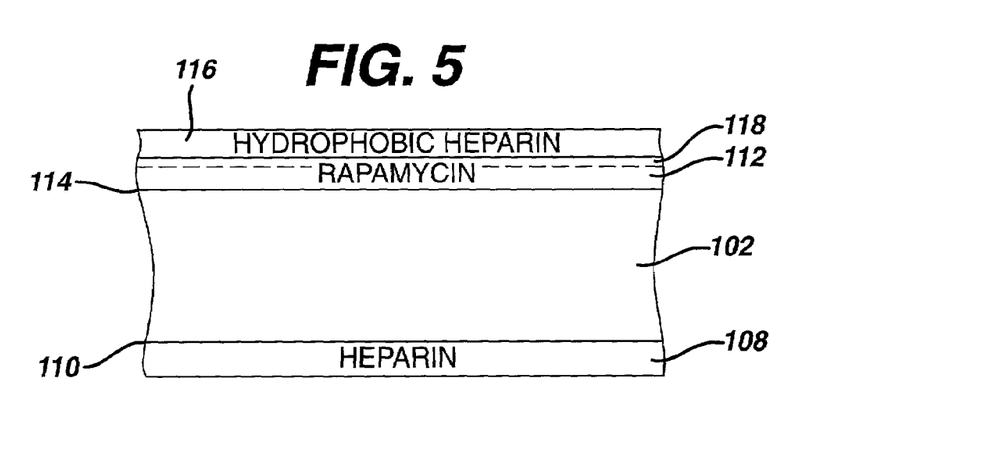
FIG. 5 is a cross-sectional view of a band of the stent of FIG. 1 having drug coatings thereon in accordance with a third exemplary embodiment of the present invention.

There are a number of possible ways to immobilize, i.e., entrapment or covalent linkage with an erodible bond, the heparin layer to the rapamycin layer. For example, heparin may be introduced into the top layer of the polymeric matrix. In other embodiments, different forms of heparin may be directly immobilized onto the top coat of the polymeric matrix, for example, as illustrated in FIG. 5. As illustrated, a hydrophobic heparin layer 116 may be immobilized onto the top coat layer 118 of the rapamycin layer 112. A hydrophobic form of heparin is utilized because rapamycin and heparin coatings represent incompatible coating application technologies. Rapamycin is an organic solvent-based coating and heparin is a water-based coating.

As stated above, a rapamycin coating may be applied to stents by a dip, spray or spin coating method, and/or any combination of these methods. Various polymers may be utilized. For example, as described above, polyethylene-co-vinyl acetate and polybutyl methacrylate blends may be utilized. Other polymers may also be utilized, but not limited to, for example, polyvinylidene fluoride-co-hexafluoropropylene and polyethylbutyl methacrylate-co-hexyl methacrylate. Also as described above, barrier or top coatings may also be applied to modulate the dissolution of rapamycin from the polymer matrix. In the exemplary embodiment described above, a thin layer of heparin is applied to the surface of the polymeric matrix. Because these polymer systems are hydrophobic and incompatible with the hydrophilic heparin, appropriate surface modifications may be required.

The application of heparin to the surface of the polymeric matrix may be performed in various ways and utilizing various biocompatible materials. For example, in one embodiment, in water or alcoholic solutions, polyethylene imine may be applied on the stents, with care not to degrade the rapamycin (e.g., pH<7, low temperature), followed by the application of sodium heparinate in aqueous or alcoholic solutions. As an extension of this surface modification, covalent heparin may be linked on polyethylene imine using amide-type chemistry (using a carbondiimide activator, e.g. EDC) or reductive amination chemistry (using CBAS-heparin and sodium cyanoborohydride for coupling). In another exemplary embodiment, heparin may be photolinked on the surface, if it is appropriately grafted with photo initiator moieties. Upon application of this modified heparin formulation on the covalent stent surface, light exposure causes cross-linking and immobilization of the heparin on the coating surface. In yet another exemplary embodiment, heparin may be complexed with hydrophobic quaternary ammonium salts, rendering the molecule soluble in organic solvents (e.g. benzalkonium heparinate, troidodecylmethylammonium heparinate). Such a formulation of heparin may be compatible with the hydrophobic rapamycin coating, and may be applied directly on the coating surface, or in the rapamycin/hydrophobic polymer formulation.

It is important to note that the stent may be formed from any number of materials, including various metals, polymeric materials and ceramic materials. Accordingly, various technologies may be utilized to immobilize the various drugs, agent, compound combinations thereon. In addition, the drugs, agents or compounds may be utilized in conjunction with other percutaneously delivered medical devices such as grafts and profusion balloons.

In addition to utilizing an anti-proliferative and anti-coagulant, anti-inflammatories may also be utilized in combination therewith. One example of such a combination would be the addition of an anti-inflammatory corticosteroid such as dexamethasone with an anti-proliferative, such as rapamycin, cladribine, vincristine, taxol, or a nitric oxide donor and an anti-coagulant, such as heparin. Such combination therapies might result in a better therapeutic effect, i.e., less proliferation as well as less inflammation, a stimulus for proliferation, than would occur with either agent alone. The delivery of a stent comprising an anti-proliferative, anti-coagulant, and an anti-inflammatory to an injured vessel would provide the added therapeutic benefit of limiting the degree of local smooth muscle cell proliferation, reducing a stimulus for proliferation, i.e., inflammation and reducing the effects of coagulation thus enhancing the restenosis-limiting action of the stent.

In other exemplary embodiments of the inventions, growth factor or cytokine signal transduction inhibitor, such as the ras inhibitor, R115777, or a tyrosine kinase inhibitor, such as tyrphostin, might be combined with an antiproliferative agent such as taxol, vincristine or rapamycin so that proliferation of smooth muscle cells could be inhibited by different mechanisms. Alternatively, an anti-proliferative agent such as taxol, vincristine or rapamycin could be combined with an inhibitor of extracellular matrix synthesis such as halofuginone. In the above cases, agents acting by different mechanisms could act synergistically to reduce smooth muscle cell proliferation and vascular hyperplasia. This invention is also intended to cover other combinations of two or more such drug agents. As mentioned above, such drugs, agents or compounds could be administered systemically, delivered locally via drug delivery catheter, or formulated for delivery from the surface of a stent, or given as a combination of systemic and local therapy.

In addition to anti-proliferatives, anti-inflammatories and anti-coagulants, other drugs, agents or compounds may be utilized in conjunction with the medical devices. For example, immunosuppressants may be utilized alone or in combination with these other drugs, agents or compounds. Also modified genes in viral and non-viral gene introducers may also be introduced locally via a medical device.

As described above, various drugs, agents or compounds may be locally delivered via medical devices. For example, rapamycin and heparin may be delivered by a stent to reduce restenosis, inflammation, and coagulation. Various techniques for immobilizing the drugs, agents or compounds are discussed above, however, maintaining the drugs, agents or compounds on the medical devices during delivery and positioning is critical to the success of the procedure or treatment. For example, removal of the drug, agent or compound coating during delivery of the stent can potentially cause failure of the device. For a self-expanding stent, the retraction of the restraining sheath may cause the drugs, agents or compounds to rub off the stent. For a balloon expandable stent, the expansion of the balloon may cause the drugs, agents or compounds to simply delaminate from the stent through contact with the balloon or via expansion. Therefore, prevention of this potential problem is important to have a successful therapeutic medical device, such as a stent.

There are a number of approaches that may be utilized to substantially reduce the above-described problem. In one exemplary embodiment, a lubricant or mold release agent may be utilized. The lubricant or mold release agent may comprise any suitable biocompatible lubricious coating. An exemplary lubricious coating may comprise silicone. In this exemplary embodiment, a solution of the silicone base coating may be introduced onto the balloon surface, onto the polymeric matrix, and/or onto the inner surface of the sheath of a self-expanding stent delivery apparatus and allowed to air cure. Alternately, the silicone based coating may be incorporated into the polymeric matrix. It is important to note, however, that any number of lubricious materials may be utilized, with the basic requirements being that the material be biocompatible, that the material not interfere with the actions/effectiveness of the drugs, agents or compounds and that the material not interfere with the materials utilized to immobilize the drugs, agents or compounds on the medical device. It is also important to note that one or more, or all of the above-described approaches may be utilized in combination.

Figure 6:
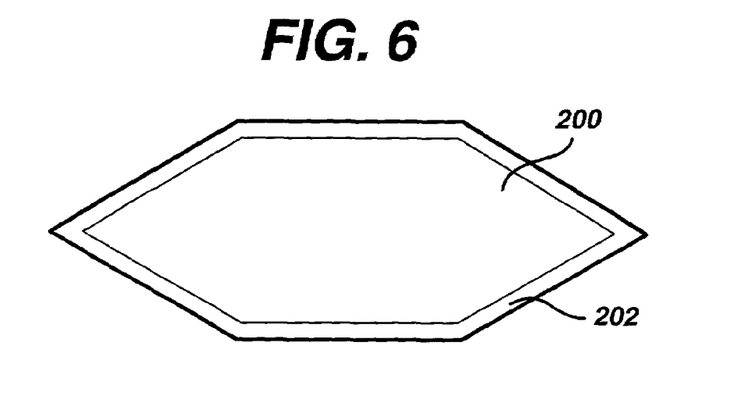
FIG. 6 is a cross-sectional view of a balloon having a lubricious coating affixed thereto in accordance with the present invention.

Referring now to FIG. 6, there is illustrated a balloon 200 of a balloon catheter that may be utilized to expand a stent in situ. As illustrated, the balloon 200 comprises a lubricious coating 202. The lubricious coating 202 functions to minimize or substantially eliminate the adhesion between the balloon 200 and the coating on the medical device. In the exemplary embodiment described above, the lubricious coating 202 would minimize or substantially eliminate the adhesion between the balloon 200 and the heparin or rapamycin coating. The lubricious coating 202 may be attached to and maintained on the balloon 200 in any number of ways including but not limited to dipping, spraying, brushing or spin coating of the coating material from a solution or suspension followed by curing or solvent removal step as needed.

Materials such as synthetic waxes, e.g. diethyleneglycol monostearate, hydrogenated castor oil, oleic acid, stearic acid, zinc stearate, calcium stearate, ethylenebis (stearamide), natural products such as paraffin wax, spermaceti wax, carnuba wax, sodium alginate, ascorbic acid and flour, fluorinated compounds such as perfluoroalkanes, perfluorofatty acids and alcohol, synthetic polymers such as silicones e.g. polydimethylsiloxane, polytetrafluoroethylene, polyfluoroethers, polyalkylglycol e.g. polyethylene glycol waxes, and inorganic materials such as talc, kaolin, mica, and silica may be used to prepare these coatings. Vapor deposition polymerization e.g. parylene-C deposition, or RF-plasma polymerization of perflouroalkenes can also be used to prepare these lubricious coatings.

Figure 7:
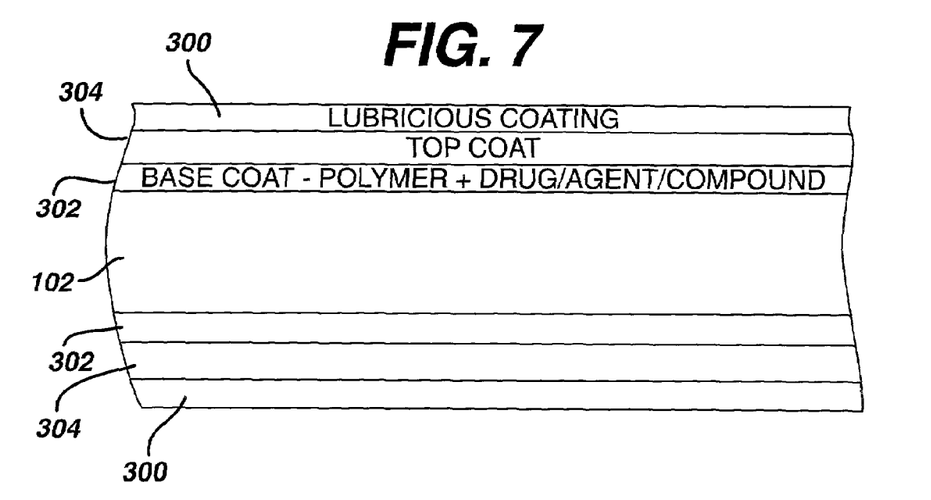
FIG. 7 is a cross-sectional view of a band of the stent in FIG. 1 having a lubricious coating affixed thereto in accordance with the present invention.

FIG. 7 illustrates a cross-section of a band 102 of the stent 100 illustrated in FIG. 1. In this exemplary embodiment, the lubricious coating 300 is immobilized onto the outer surface of the polymeric coating. As described above, the drugs, agents or compounds may be incorporated into a polymeric matrix. The stent band 102 illustrated in FIG. 7 comprises a base coat 302 comprising a polymer and rapamycin and a top coat 304 or diffusion layer 304 also comprising a polymer. The lubricious coating 300 is affixed to the top coat 302 by any suitable means, including but not limited to spraying, brushing, dipping or spin coating of the coating material from a solution or suspension with or without the polymers used to create the top coat, followed by curing or solvent removal step as needed. Vapor deposition polymerization and RF-plasma polymerization may also be used to affix those lubricious coating materials that lend themselves to this deposition method, to the top coating. In an alternate exemplary embodiment, the lubricious coating may be directly incorporated into the polymeric matrix.

Figure 8:
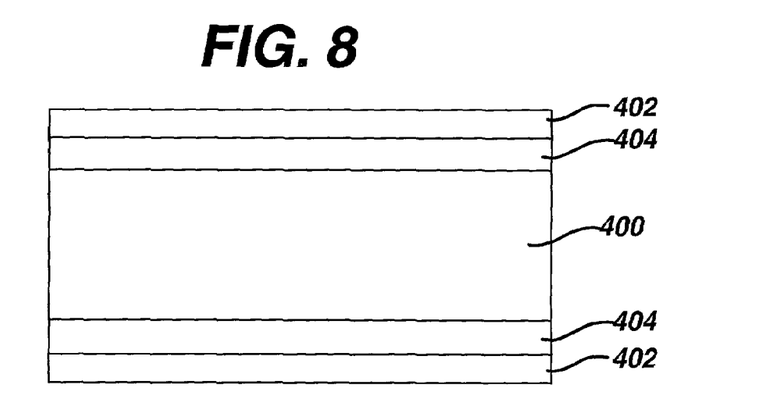
FIG. 8 is a cross-sectional view of a self-expanding stent in a delivery device having a lubricious coating in accordance with the present invention.

If a self-expanding stent is utilized, the lubricious coating may be affixed to the inner surface of the restraining sheath. FIG. 8 illustrates a self-expanding stent 400 within the lumen of a delivery apparatus sheath 402. As illustrated, a lubricious coating 404 is affixed to the inner surfaces of the sheath 402. Accordingly, upon deployment of the stent 400, the lubricious coating 404 preferably minimizes or substantially eliminates the adhesion between the sheath 402 and the drug, agent or compound coated stent 400.

Figure 9:
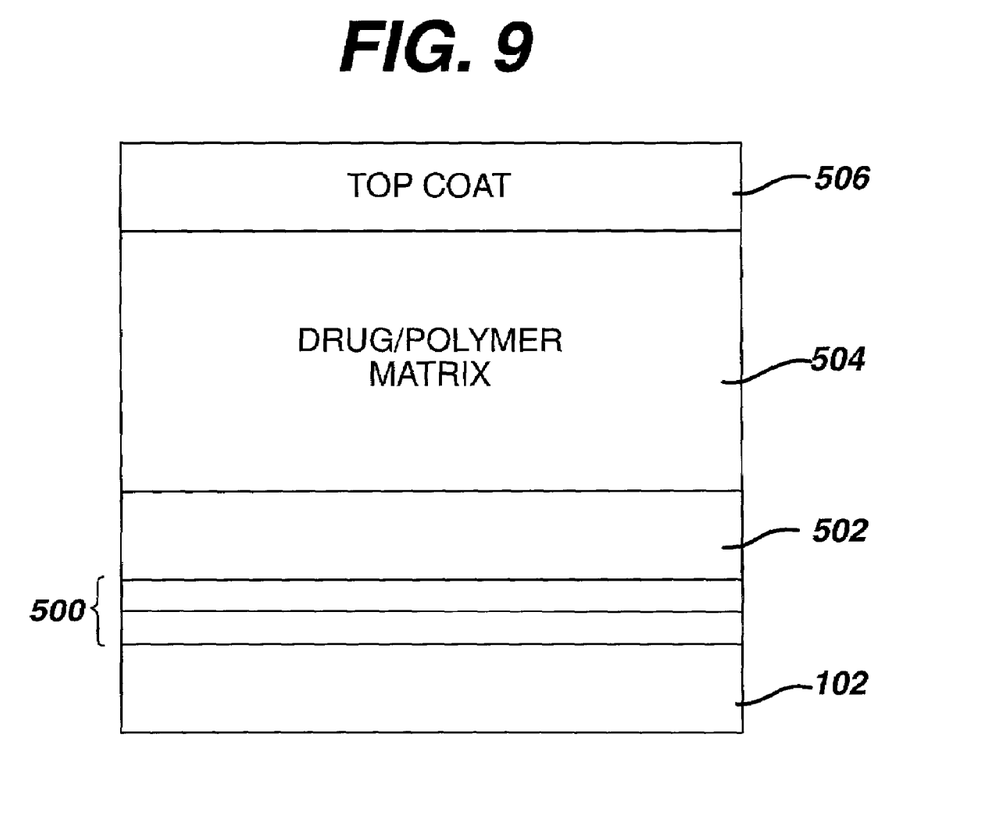
FIG. 9 is a cross-sectional view of a band of the stent in FIG. 1 having a modified polymer coating in accordance with the present invention.

In an alternate approach, physical and/or chemical cross-linking methods may be applied to improve the bond strength between the polymeric coating containing the drugs, agents or compounds and the surface of the medical device or between the polymeric coating containing the drugs, agents or compounds and a primer. Alternately, other primers applied by either traditional coating methods such as dip, spray or spin coating, or by RF-plasma polymerization may also be used to improve bond strength. For example, as shown in FIG. 9, the bond strength can be improved by first depositing a primer layer 500 such as vapor polymerized parylene-C on the device surface, and then placing a second layer 502 which comprises a polymer that is similar in chemical composition to the one or more of the polymers that make up the drug-containing matrix 504, e.g., polyethylene-co-vinyl acetate or polybutyl methacrylate but has been modified to contain cross-linking moieties. This secondary layer 502 is then cross-linked to the primer after exposure to ultraviolet light. It should be noted that anyone familiar with the art would recognize that a similar outcome could be achieved using cross-linking agents that are activated by heat with or without the presence of an activating agent. The drug-containing matrix 504 is then layered onto the secondary layer 502 using a solvent that swells, in part or wholly, the secondary layer 502. This promotes the entrainment of polymer chains from the matrix into the secondary layer 502 and conversely from the secondary layer 502 into the drug-containing matrix 504. Upon removal of the solvent from the coated layers, an interpenetrating or interlocking network of the polymer chains is formed between the layers thereby increasing the adhesion strength between them. A top coat 506 is used as described above.

A related problem occurs in medical devices such as stents. In the drug-coated stents crimped state, some struts come into contact with each other and when the stent is expanded, the motion causes the polymeric coating comprising the drugs, agents or compounds to stick and stretch. This action may potentially cause the coating to separate from the stent in certain areas. The predominant mechanism of the coating self-adhesion is believed to be due to mechanical forces. When the polymer comes in contact with itself, its chains can tangle causing the mechanical bond, similar to Velcro®. Certain polymers do not bond with each other, for example, fluoropolymers. For other polymers, however, powders may be utilized. In other words, a powder may be applied to the one or more polymers incorporating the drugs, agents or other compounds on the surfaces of the medical device to reduce the mechanical bond. Any suitable biocompatible material which does not interfere with the drugs, agents, compounds or materials utilized to immobilize the drugs, agents or compounds onto the medical device may be utilized. For example, a dusting with a water soluble powder may reduce the tackiness of the coatings surface and this will prevent the polymer from sticking to itself thereby reducing the potential for delamination. The powder should be water-soluble so that it does not present an emboli risk. The powder may comprise an anti-oxidant, such as vitamin C, or it may comprise an anti-coagulant, such as aspirin or heparin. An advantage of utilizing an anti-oxidant may be in the fact that the anti-oxidant may preserve the other drugs, agents or compounds over longer periods of time.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A local drug delivery apparatus comprising:
   a medical device for implantation into a treatment site of a living organism;
   a layer including a rapamycin in therapeutic dosages incorporated in a polymeric matrix and affixed to the medical device for the treatment of reactions by the living organism caused by the medical device or the implantation thereof; and
   a distinct and separate biocompatible, water soluble powder layer applied to an outermost surface of the polymeric matrix configured to prevent the layer affixed to the medical device from separating from the medical device prior to implantation of the medical device at the treatment site, the water-soluble powder comprising an anti-oxidant.

2. The local drug delivery apparatus according to claim 1, wherein the medical device comprises an intraluminal medical device.

3. The local drug delivery apparatus according to claim 2, wherein the intraluminal medical device comprises a stent.

* * * * *